United States Patent [19]

Rogers

[11] Patent Number: 4,568,432

[45] Date of Patent: Feb. 4, 1986

[54] PROCESS FOR PREPARING GLYPHOSATE AND GLYPHOSATE DERIVATIVES

[75] Inventor: Thomas E. Rogers, Manchester, Mo.

[73] Assignee: Monsanto Company, St. Louis, Mo.

[21] Appl. No.: 687,309

[22] Filed: Dec. 28, 1984

[51] Int. Cl.⁴ ................................................. C25B 3/00
[52] U.S. Cl. ..................................... 204/73 R; 204/75; 204/76; 260/502.5 F; 260/502.5 B; 260/501.12
[58] Field of Search .......................... 204/73 R, 75, 76; 260/502.5 F, 502.5 B, 501.12

[56] References Cited

U.S. PATENT DOCUMENTS 3,288,846 11/1966 Irani .............................. 260/502.5 F
4,233,056 11/1980 Maier ............................ 260/502.5 F

*Primary Examiner*—John F. Niebling
*Attorney, Agent, or Firm*—Raymond C. Loyer; Frank D. Shearin

[57] ABSTRACT

A process for preparing glyphosate and derivatives of related structure. A precursor primary or secondary amine, such as glycine, is condensed with a carbonyl compound, such as formylphosphonic acid or its acetals, and the condensation product is reduced to produce the desired product.

21 Claims, 3 Drawing Figures

PROCESS FOR PREPARING GLYPHOSATE AND GLYPHOSATE DERIVATIVES

BACKGROUND OF THE INVENTION

This invention relates to the synthesis of secondary and tertiary amines containing phosphonyl and carbonyl groups and, more particularly, to an improved process for producing N-phosphonomethylglycine or derivatives thereof by reductive alkylation.

N-Phosphonomethylglycine, known in the agricultural chemical art as glyphosate, is a highly effective and commercially important phytotoxicant useful in controlling the growth of germinating seeds, emerging seedlings, maturing and established woody and herbaceous vegetation, and aquatic plants. Glyphosate and salts thereof are conveniently applied in the form of an aqueous solution as a post-emergent phytotoxicant or herbicide for the control of growth of one or more monocotyledonous species and one or more dicotyledonous species. Moreover, such compounds are characterized by broad spectrum activity, i.e., they control the growth of a wide variety of plants, including but not limited to ferns, conifers, aquatic monocotyledons, and dicotyledons.

Hershman, U.S. Pat. No. 3,969,398, describes a process for preparing glyphosate in which iminodiacetic acid is reacted with formaldehyde and phosphorous acid to produce N-phosphonomethyliminodiacetic acid as an intermediate. This is then oxidized to produce glyphosate.

Gaertner, Canadian Pat. No. 1,039,739, describes a process for producing glyphosate by reacting aminomethylphosphonic acid and esters with glyoxal or glyoxylic acid to form a carbonylaldiminomethanephosphonate. Thereafter, the carbonylaldiminomethanephosphonate is subjected to catalytic hydrogenation to reduce the double bond and produce glyphosate or esters. The ester groups are then hydrolyzed to produce N-phosphonomethylglycine. Both the condensation of aminomethylphosphonate with aldehyde and catalytic hydrogenation of the resultant imine are carried out in organic solvents. For the condensation reaction, the solvent is an aromatic hydrocarbon, such as benzene, toluene, or xylene, while catalytic hydrogenation is typically carried out in an alcohol.

Franz, U.S. Pat. No. 3,799,758, describes the preparation of glyphosate by reaction of ethyl glycinate, formaldehyde, and diethyl phosphite. Alternative processes described by Franz include phosphonomethylation of glycine with chloromethylphosphonic acid in the presence of sodium hydroxide and oxidation of N-phosphinomethylglycine with mercuric chloride.

Gaertner, U.S. Pat. No. 3,927,080, describes the production of glyphosate by acid hydrolysis of N-t-butyl-N-phosphonomethylglycine or its esters. Tertiary butyl amine is reacted with a bromoacetate ester to produce an ester of N-t-butylglycine which is in turn reacted with formaldehyde and phosphorous acid to produce the N-t-butyl-N-phosphonomethylglycine precursor.

Ehrat, U.S. Pat. No. 4,237,065, describes a process in which glycine is condensed with formaldehyde in the presence of a tertiary base to produce N-methyl glycine or N-methylene glycine, and the latter is in turn reacted with phosphorous acid to produce glyphosate.

Pfliegle et al, U.S. Pat. No. 4,065,491, discloses a process in which N-phosphonomethylglycine is prepared by condensation of glycine, formaldehyde, and a dialkyl phosphite in an aqueous alkaline medium to form an N-phosphonomethylglycine dialkyl ester. The latter is hydrolyzed with a mineral acid to produce glyphosate.

While Gaertner, as described in his aforesaid Canadian patent, achieved monoalkylation of aminomethylphosphonic acid by the sequential process of first condensing aminomethylphosphonic acid or its esters with glyoxylic acid or its esters to produce the aldimine and thereafter subjecting the aldimine to catalytic hydrogenation, there are other references which describe the in situ reduction of the condensation products of various amines and aldehydes. Such condensation and in situ reduction is generally referred to in the art as reductive alkylation. However, when the aldimino structure obtained by condensation of a primary amine with an aldehyde is reduced in situ, the resultant secondary amine can further react with the aldehyde to produce an aminal which is in turn reduced by hydrogenolysis resulting in formation of a tertiary amine. Thus, the result is typically substantial dialkylation rather than the substantially exclusive monoalkylation that is preferred in the preparation of an end product, such as glyphosate.

Ikutani, "Studies of the N-Oxides of N,N-Dialkyl Amino Acids. II. The Syntheses of N,N-Dialkylglycine and Corresponding N-Oxides", *Bulletin of the Chemical Society of Japan*, 42, pp. 2230–2332, (1969) reports the reductive condensation of glycine with various aliphatic aldehydes. Only with relatively hindered aldehydes did Ikutani recover any monoalkylated product after reactions at 40° C. to 50° C. for periods of 3 to 9 hours. In the case of acetaldehyde, propionaldehyde, and n-butyraldehyde, at best a trace of monoalkyl product was recovered while the dialkyl yields ranged from 41% to 83%.

Bowman, "N-Substituted Amino Acids. Part II. The Reductive Alkylation of Amino Acids", *Journal of the Chemical Society*, Part 2, p. 1346, (1950) reported that experiments on the alkylation of glycine by means of acetaldehyde, propionaldehyde, n-butanal, and n-heptanal, under conditions favorable to the formation of monoalkyl derivatives, failed to reveal any evidence of partial alkylation.

Moser, U.S. Pat. No. 4,369,142, describes a process for the preparation of N-phosphonomethylglycine in which aminomethylphosphonic acid is reacted in aqueous medium with glyoxal in the presence of sulfur dioxide.

In DE No. 2,725,669 there is disclosed a process for the preparation of secondary amines under hydrogenation conditions in the presence of a catalyst comprising nickel or cobalt and a quaternary ammonium compound. High yields are reported.

Mono-substituted amino acids, such as glycines and alanines, are prepared by a process disclosed in EPO No. 0079767 wherein a primary amino group and a ketone are reacted under reductive condensation conditions in the presence of a reductant and a hydrogenation catalyst under conditions of elevated temperature and superatmospheric conditions. Nobel metal catalysts are described and the preferred catalyst is palladium on carbon.

SUMMARY OF THE INVENTION

The present invention relates to a process for preparing glyphosate and glyphosate derivatives corresponding to the Formula (I)

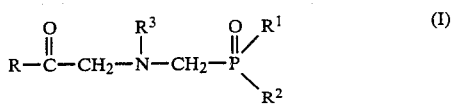

wherein R can be hydrogen and R, $R^1$, and $R^2$ are independently selected from the group consisting of —OH; —SH;

—$NR^4R^5$ wherein $R^4$ and $R^5$ are independently selected from the group consisting of hydrogen, alkyl, and hydroxyalkyl having 1 through 4 carbon atoms, alkenyl having 2 through 4 carbon atoms, and $R^4$ and $R^5$ together with the nitrogen atoms can form a heterocyclic ring;

—$OR^6$ and $SR^6$ wherein $R^6$ is selected from the group consisting of monovalent hydrocarbon groups, monovalent hydrocarbonoxyhydrocarbon groups each containing from 1 to 18 carbon atoms, halogenated monovalent hydrocarbon groups, halogenated monovalent hydrocarbonoxyhydrocarbon groups each containing from 1 to 18 carbon atoms and from 1 to 3 halogens, and groups having the formula

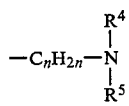

wherein n is from 1 to 4, and $R^4$ and $R^5$ are as defined above;

—$OR^7$ wherein $R^7$ is a herbicidally acceptable salt-forming cation; and $R^3$ is hydrogen or alkyl.

The term monovalent hydrocarbon as used herein includes alkyl, alkenyl, alkynyl, aralkyl inclusive of both straight and branched chain radicals, such as methyl, ethyl, isopropyl, cyclopropyl, cyclohexyl, tertiary butyl, iso-butyl, n-butyl, and the various forms amyl, hexyl, heptyl, octyl, nonyl, decyl, undecyl, dodecyl, tridecyl, tetradecyl, pentadecyl, hexadecyl, heptadecyl, octadecyl, benzyl, phenylethyl, naphthylethyl, tolylethyl, methylbenzyl, phenylbenzyl and the corresponding alkenyl, and alkynyl groups and the like, aryl groups and alkaryl groups, such as phenyl, tolyl, xylyl, naphthyl, vinylphenyl and the like. It is preferred that such monovalent hydrocarbon group contains from 1 to 18 carbon atoms and be alkyl, alkenyl, or alkynyl groups.

The monovalent hydrocarbonoxyhydrocarbon groups represented by $R^6$ include alkoxyalkyl, alkenoxyalkyl, aryloxyalkyl and alkoxyaryl, such as 2-methoxyethyl, 4-ethoxy-2-methylbutyl, 2-ethoxyethyl, 3-propoxypropyl, 4-methoxybutyl, 4-methoxy-2-ethylbutyl, 4-butoxybutyl, 2-allyloxyethyl, 2-butenoxyethyl, 4-butenoxybutyl, 4-(3-methoxypropoxy)butyl, 2-(3-allyloxypropoxy)-ethyl, phenoxyethyl, naphthoxyethyl, butyl, 2,4-diethoxyphenyl, 2-methoxyphenyl, tolyloxyethyl, 4-phenoxybutyl, trifluoromethylphenyl and the like.

Illustrative of the halogenated monovalent hydrocarbon groups represented by $R^6$ are haloalkyl, such as chloromethyl, iodomethyl, bromomethyl, fluoromethyl, chloroethyl, iodoethyl, bromoethyl, 1,2-dichloroethyl, 1,2-diiodoethyl, chloro-n-propyl, bromo-n-propyl, iodoisopropyl, bromo-n-butyl, bromotertbutyl, 1,3,3-trichlorobutyl, chloropentyl, bromopentyl, 2,3-dichloropentyl, chlorohexyl, bromohexyl, 2,4-dichlorohexyl, 1,3-dibromohexyl, 1,3,4-trichlorohexyl, chloroheptyl, bromo-heptyl, fluoroheptyl, 1,3-dichloroheptyl, 1,4,4-trichloro-heptyl, 2,4-dichloromethyl-heptyl, chlorooctyl, bromooctyl, iodooctyl, 2,4-dichloromethylhexyl, 2,4-dichlorooctyl, 2,4,4-trichloromethylpentyl, 1,3,5-tribromooctyl and the halogenated straight and branched chain nonyl, decyl, undecyl, dodecyl, tridecyl, tetradecyl, pentadecyl, hexadecyl, heptadecyl and octadecyl; haloalkenyl, such as chlorovinyl, bromovinyl, chloroallyl, bromoallyl, 3-chloro-n-butenyl-1, 3-chloro-n-pentenyl-1, 4-chloro-n-hexenyl-2, 3,4-dichloromethyl-pentenyl-1, 3-fluoro-n-heptenyl-1, 1,3,3-trichloro-n-heptenyl-5, 1,3,5-trichloro-n-octenyl-6, 2,3,3-trichloromethylpentenyl-4 and the various homologues and isomers of haloalkenyl having 2 to 12 carbon atoms; haloaryl, such as o-chlorophenyl, 2,4-dichlorophenyl, 3,5-dichlorophenyl, 2,5-diiodophenyl and the like. The halogenated monovalent hydrocarbonoxyhydrocarbon groups represented by $R^6$ are the alkoxy and aryloxy substituted derivatives of the foregoing halogenated monovalent hydrocarbon groups where the alkyl and aryl groups are those previously set forth.

The term "aryl" as employed herein includes phenyl, naphthyl, and biphenylyl. The term "substituted aryl" as employed herein includes phenyl, naphthyl, and biphenylyl substituted with from 1 to 3 substituents independently selected from the class comprising lower alkyl, lower alkoxy, lower alkylthio, alkoxycarbonyl, trifluoromethyl, cyano, nitro, and halogen, i.e., chlorine, bromine, fluorine, and iodine. Of course, certain substituents may present steric hindrance such that adjacent positions on the aryl ring are not occupied but such variation is well understood by those skilled in the art.

Illustrative of the substituted phenyl groups are mono-substituted phenyl wherein the substituent is in the ortho, meta, or para position, for example, methylphenyl, butylphenyl, methoxyphenyl, butoxyphenyl, fluorophenyl, chlorophenyl, bromophenyl, iodophenyl, trifluoromethylphenyl, nitrophenyl, methylthiophenyl, butylthiophenyl, cyanophenyl, ethoxycarbonylphenyl and the like, and the di- and tri-substituted phenyl groups wherein the substituents are the same or different and are located in the 2, 3, 4, 5, or 6 positions of the phenyl ring, for example, dichlorophenyl, dimethylphenyl, methylchlorophenyl, ethylfluorophenyl, dibutoxyphenyl, butylnitrophenyl, methylthiochlorophenyl, di(ethyl-thio)phenyl, trimethylphenyl, trichlorophenyl, tributylphenyl, ethyldichlorophenyl and the like.

Groups representative of a substituted naphthyl group include methylnaphthyl, nitronaphthyl, bromonaphthyl, dimethylnaphthyl, difluoronaphthyl, trimethylnaphthyl and the like.

Groups representative of substituted biphenylyl include methylbiphenylyl, nitrobiphenylyl, bromobiphenylyl, dimethylbiphenylyl, difluorobiphenylyl, trimethylbiphenylyl and the like.

Illustrative of herbicidally acceptable salt-forming cations (but not limited to) are alkali metals, alkaline earth metals, copper, zinc, manganese, nickel, ammonium, aliphatic ammonium, phosphonium, aliphatic phosphonium, aliphatic sulfonium, and primary aryl ammonium. Preferably the salt-forming cation renders glyphosate or glyphosate derivatives more readily soluble in water. Salt-forming cations which function so as to render glyphosate or glyphosate derivatives more readily soluble in water typically include but are not limited to alkali metals, ammonium, organic ammonium, and aliphatic sulfonium.

The $R^3$ alkyl substituent employed in the process of this invention typically includes and is not limited to any cyclic, straight, or branched chain alkyl group, such as methyl, ethyl, propyl, isopropyl, butyl, hexyl, cyclohexyl, and cyclopropyl. The preferred alkyl substituent is represented by the formula

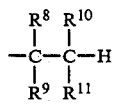

wherein $R^8$, $R^9$, $R^{10}$, and $R^{11}$ are independently selected from the group consisting of hydrogen, alkyl $C_{1-6}$, aryl, and substituted aryl provided no more than two of $R^8$, $R^9$, $R^{10}$, and $R^{11}$ are aryl or substituted aryl.

In the process, a precursor primary or secondary amine corresponding to Formula (II)

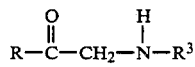   (II)

where R and $R^3$ are as defined above, is condensed in an aqueous medium with a carbonyl compound or hydrate or acetal thereof. The carbonyl compound corresponds to Formula (III) or (IV)

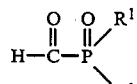   (III)

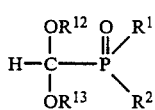   (IV)

wherein $R^1$ and $R^2$ are as defined above, $R^{12}$ and $R^{13}$ are independently selected from hydrogen, alkyl, hydroxyalkyl having 1 to 4 carbon atoms, alkenyl and alkyl having 2 to 4 carbon atoms joined through the oxygen atoms to form a cyclic acetal, aryl, substituted aryl, or heterocyclic moieties. The condensation product is reduced in situ to produce the desired compound of Formula (I).

DESCRIPTION OF THE PREFERRED EMBODIMENT

The present invention resides in the discovery that glyphosate and various glyphosate derivatives can be produced with very high selectivity by the reductive alkylation of glycine, its salts, or its esters, in an aqueous medium with a carbonyl compound, such as formylphosphonic acid, its hydrate, or its acetals. Contrary to the results reported for the reductive alkylation of glycine with linear aldehydes, such as acetaldehyde or butyraldehyde, high conversions of the reactants to the monoalkylated product can be achieved with relatively minimal dialkylation. Thus, not only high selectivity but good overall yields are obtained. In the aqueous reaction medium, reduction of the intermediate reaction product is carried either by catalytic hydrogenation or electrochemical reduction.

By use of the reaction scheme of the invention, a wide variety of products can be produced having structures generally patterned on or comparable to glyphosate. Although the process of the invention is particularly advantageous for the monoalkylation of certain primary amines to secondary amines, it may also be used for the monoalkylation of secondary amines to tertiary amines. Thus, the amine reactant in the process of the invention may be generally defined as

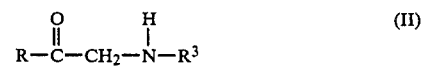   (II)

where R and $R^3$ are as defined above. In cases where R, $R^1$, and $R^2$ can be $OR^7$, $R^7$, in addition to other values, may be a herbicidally acceptable salt-forming cation selected from, for example, the groups consisting of alkali metals, alkaline earth metals, copper, zinc, manganese, nickel, ammonium, aliphatic ammonium, phosphonium, aliphatic phosphonium, aliphatic sulfonium, and primary aryl ammonium.

The carbonyl compound used in the reductive alkylation of the amines (II) conforms to the Formula (III) and (IV) above.

Generally, R, $R^1$, $R^2$, and $R^3$ should not include moieties which are reactive with each other to any significant extent under the conditions of the reductive alkylation, nor should these groups include moieties preferentially reactive under such conditions with either the amine or carbonyl group involved in the reductive alkylation.

Thus, the product corresponds generally to the Formula (I)

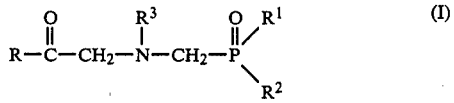   (I)

where R, $R^1$, $R^2$, and $R^3$ are as defined above.

In accordance with the process of the invention, the amine compound of Formula (II) (for example, glycine) and the carbonyl compound of Formula (III) (for example, formylphosphonic acid) are dissolved in an aqueous medium and thereafter reacted under reducing conditions either via catalytic hydrogenation or electrochemical reduction. Where the amine compound is a primary amine, the reaction proceeds through condensation of amine and carbonyl compound to form the intermediate, followed by reduction thereof without isolation to produce the final product. The process of this invention can also be used for producing tertiary amines by reductive alkylation of secondary amines.

Figure 1:
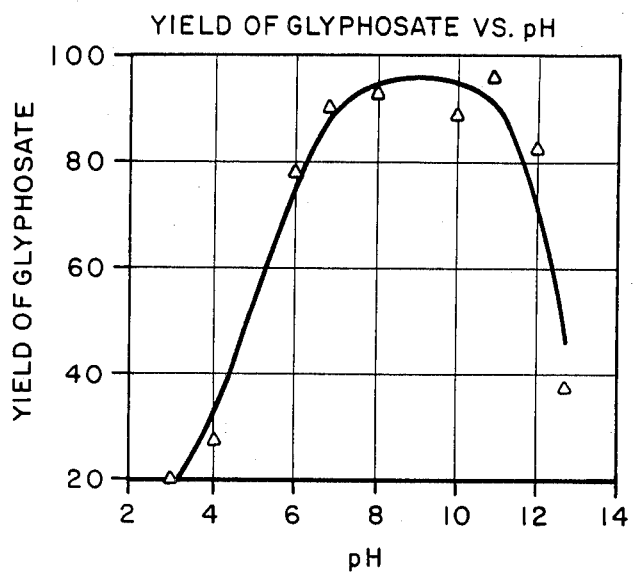
FIG. 1 is a plot of yield of monoalkylated product as a function of the pH of the reaction medium.

Preferably, the pH of the aqueous solution containing the amine and carbonyl compound reactants is adjusted to between about 5.5 and about 12.0, preferably 7.0 to 12.0, prior to carrying out the reductive alkylation. The mechanism by which pH affects the productivity of the reaction is not known. However, the condensation reaction is understood to be reversible and it is, therefore, believed that a pH more acid than 5.5 may adversely affect the equilibrium constant for this reaction. Conditions more acid than pH 5.5 and those more alkaline than pH 12.0 may conduce to the reduction of the aldehyde to the hydroxyalkyl phosphonic acid and/or to poor selectivity. FIG. 1 illustrates the influence of pH on selectivity in the preparation of glyphosate (or its sodium salts) by reaction of glycine and formylphosphonic acid.

Adjustment of pH is carried out by addition of a base, typically an alkali metal hydroxide, such as sodium hydroxide or potassium hydroxide. Tertiary amines, such as triethylamine, may also be used as well as primary and secondary amines. After adjustment of pH, the aqueous solution is either contacted with hydrogen in the presence of a hydrogenation catalyst or placed in an electrochemical cell where the intermediate formed by the condensation reaction is cathodically reduced.

In the case of catalytic hydrogenation, a wide variety of hydrogenation catalysts may be used including various platinum group metals, such as platinum, palladium, iridium, osmium, rhodium, or ruthenium and various other transition metals, such as nickel and cobalt. Other metals, such as copper and zinc, can also be used. Either elemental metals or various compounds of such metals, such as oxides, halides, and organometallics, can be used. Where the catalyst is a solid state material, it can be either supported, such as, for example, platinum on carbon, palladium on alumina, nickel on kieselguhr, etc., or unsupported, for example, Raney nickel or platinum oxide. Various soluble compounds of catalytic metals can also be employed. Palladium on carbon and Raney nickel are particularly effective and convenient catalysts and thus somewhat preferred. But depending on the conditions and nature of the substrate, a number of other catalysts may be equally effective.

The preferred concentration of catalyst also varies widely depending on substrate and conditions. However, the optimum proportion for any particular system can be readily arrived at by routine testing.

Pressure is not generally a highly critical variable where the reductive alkylation of the invention is carried out by catalytic hydrogenation. Pressure can be varied widely. For convenience, however, hydrogen pressures from atmospheric to about $4.60 \times 10^8$ Newtons/meter$^2$ (N/m$^2$) or more are used.

In order to achieve high selectivity in monoalkylation of primary amines, it has not been found necessary to operate with any significant excess of the amine reactant. Substantially equimolar proportions can be used and, in fact, a slight excess of carbonyl compound, for example, a carbonyl/amine molar ratio of 1.0 to 1.2, is generally preferred. The concentration of each reactant may vary over a wide range. For convenience, however, reactant concentrations ranging from 2% to 20% by weight are preferred.

In the case of electrochemical reduction, concentrations of reactants and pH are governed by essentially the same considerations discussed above. To carry out the electrochemical reductive alkylation, the solution of amine and carbonyl compound is placed in an electrolytic cell, preferably as the catholyte in a cell having a porous barrier between catholyte and anolyte chambers. Such a cell is illustrated, for example, in FIG. 2. This cell includes a container 1 having a porous alumina cup 3 disposed therein. Inside cup 3 is a platinum mesh anode 5. A mercury pool 7, covering the bottom wall 9 of container 1, serves as the cathode. Cup 3 thus divides the cell into anolyte chamber 11 and catholyte chamber 13, respectively. In operating this cell, any convenient electrolyte can be used for the anolyte. Current is applied preferably at a density of approximately 0.001 to 0.5 amps per square centimeter to effect the reduction.

Figure 2:
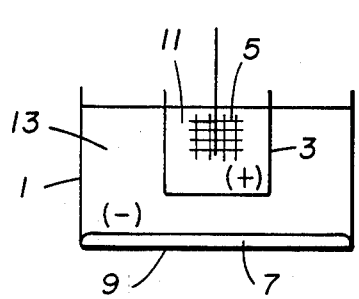
FIG. 2 is a schematic drawing illustrating a cell in which the process of the invention can be carried out via electrochemical reduction.

Electrolytic reduction may also be carried out in an undivided cell, whose construction may be essentially identical to that of FIG. 2 except that cup 3 is absent and no separate anolyte liquor is used.

Figure 3:
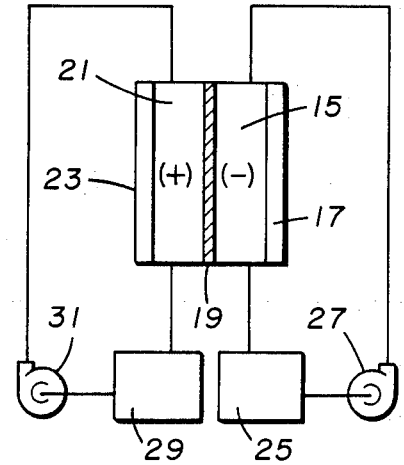
FIG. 3 is a schematic drawing illustrating an alternative cell for carrying out the process of the invention via electrochemical reduction.

Alternatively, electrochemical reduction can take place in a flow cell, such as that illustrated in FIG. 3. In this cell a catholyte flow channel 15 is disposed between a cathode 17 and a semi-permeable membrane 19 which comprises an ion exchange resin. Reaction solution contained in a reservoir 25 is continuously passed through catholyte channel 15 by means of a pump 27. On the opposite side of membrane 19 from channel 15 is an anolyte chamber 21 and a carbon anode 23. Anolyte solution contained in reservoir 29 is continuously passed through anolyte channel 21 by means of a pump 31.

The cathode of the electrochemical reduction cell is preferably comprised of a material which exhibits a high hydrogen overpotential in the electrochemical reduction system. Such include, for example, mercury, cadmium, lead, palladium, platinum, or graphite. Selection of the anode material is not particularly critical. Thus, for example, the anode may be of platinum, carbon, graphite, platinized titanium, stainless steel, etc.

Products produced in accordance with the reductive alkylation reaction of this invention may have a variety of uses, but they are particularly useful as herbicides.

Product may be recovered from the reaction solution by various conventional methods. Where the reductive alkylation is conducted by catalytic hydrogenation using a solid state catalyst, the first step in product recovery is removal of the catalyst, as by filtration or centrifugation. The recovered catalyst may in most instances be recycled and reslurried with fresh feed solution containing amines and carbonyl compound reactants.

Once the reaction solution is clarified, reaction product may be separated, for example, by evaporation. However, in the case of glyphosate or its salts, the product need not be recovered and the solution can be used directly as a herbicide, if desired.

Formylphosphonic acid for use in practicing the process of this invention can be conveniently prepared as described by Wagenknecht, *Journal of Electrochemical Society*, Vol. 123, pp. 620-624 (May, 1976) and in Bayer U.S. Pat. No. 4,348,332, the teachings of which are incorporated herein by reference.

The process of this invention is further illustrated by the following examples.

EXAMPLE 1

Formylphosphonic acid (2 g) was taken up in water (50 ml) and the pH of the resultant solution adjusted to 5.8 by portionwise addition of sodium carbonate. The formylphosphonic acid solution was then added dropwise to a solution of glycine (4 g) in water (20 ml) at room temperature. Dissolved carbon dioxide was removed under vacuum, and the decarbonated solution and a 2.5% platinum on carbon catalyst (1 g) were placed in a pressure bottle having a magnetic stirrer. The pressure bottle was sealed and pressurized with hydrogen to $3.45 \times 10^5$ N/m² gauge. During the subsequent hydrogenation reaction, the hydrogen was periodically replenished by repressurizing the bottle to $3.45 \times 10^5$ N/m² gauge. After 50 hours reaction at room temperature, water was removed from the reaction solution under vacuum, leaving a light yellow glass which was analyzed by nuclear magnetic resonance. Comparison with known NMR characteristics of N-phosphonomethylglycine confirmed the presence of a significant proportion of this product in the yellow glass residue.

EXAMPLE 2

To a 59% aqueous formylphosphonic acid solution (5.0 g; 0.23 mol) in deionized water (25 ml) was added glycine (1.56 g; 0.021 mol). The pH of the resultant mixture was adjusted to 7.0 by addition of 2.5N sodium hydroxide. The reaction mixture was then transferred to a 300 ml autoclave, a 10% palladium on carbon catalyst (1.0 g) added, and the reactor sealed and pressurized with hydrogen to $6.89 \times 10^6$ N/m² gauge. After 60 minutes of reaction at room temperature, 3.2 g of N-phosphonomethylglycine was obtained representing a 91% yield on glycine.

Similarly, N-methylglyphosate can be prepared by reacting equimolar amounts of N-methylglycine and formylphosphonic acid according to the conditions of Example 2. Upon the cessation of hydrogen uptake, a substantial amount of N-methylglyphosate will have been produced.

Also N-isopropylglyphosate can be prepared by reacting equimolar amounts of N-isopropylglycine and formylphosphonic acid according to the conditions of Example 2. Upon cessation of hydrogen uptake, a substantial amount of N-isopropylglyphosate will have been produced.

EXAMPLE 3

N-phosphonomethylglycine was produced in the manner described in Example 2 except that the amount of glycine charged was 1.9 g (0.025 mol), the pH was adjusted to 6.0 prior to hydrogenation, and the catalyst for the hydrogenation was 60% nickel on kieselguhr (0.20 g). After 3 hours and 30 minutes of reaction at room temperature, the reactor was sampled, and it was determined that 2.71 g of N-phosphonomethylglycine had been produced, a yield of 69.4% based on formylphosphonic acid. The reaction was thereafter allowed to continue overnight, after which the N-phosphonomethylglycine produced was 3.0 g, a 78% yield.

EXAMPLE 4

N-phosphonomethylglycine was produced in the manner described in Example 2 except that the pH was adjusted prior to hydrogenation, and the hydrogenation catalyst was No. 28 Davison Raney Nickel (3.0 g). After 3 hours and 15 minutes, a 76% yield of N-phosphonomethylglycine was obtained.

EXAMPLE 5

N-phosphonomethylglycine was produced in the manner described in Example 4 except that the reaction was carried out at a temperature of 40° C. After 2 hours a 73% yield of the desired product was obtained.

EXAMPLE 6

Reaction of glycine and formylphosphonic acid was carried out in the manner described in Example 2 except that the amount of glycine used was increased slightly (1.9 g; 0.025 mole), a smaller amount of catalyst was supplied (0.1 g), and the pH was adjusted to 8.0. The system was maintained at the reaction temperature and pressure for 20 hours although hydrogen uptake ceased after 0.5 hour. The analysis indicated a 93.9% yield of glyphosate salt.

EXAMPLE 7

The conditions of Example 6 were repeated except that the hydrogen pressure was increased to $3.17 \times 10^7$ N/m². Reaction was terminated after 3 hours. Analysis revealed a 58.1% yield of glyphosate.

EXAMPLE 8

Reaction was carried out under the conditions of Example 6 except that the diethyl acetal of formylphosphonic acid (4.4 g; 0.024 mole) was used in place of formylphosphonic acid and the reaction temperature was 60° C. Reaction was continued for 20 hours. A 63% yield of glyphosate salt was obtained.

EXAMPLE 9

Reaction was carried out in the manner described in Example 6 except that the pH was adjusted to 11.0. Analysis of the product indicated a 95% yield of glyphosate salt.

EXAMPLE 10

Reaction of formylphosphonic acid and glycine was carried out under the conditions described in Example 6 except that the pH was adjusted to 10.0 before commencement of the reduction reaction. Analysis indicated a 90.0% yield of glyphosate salts.

EXAMPLE 11

Reaction was carried out under the conditions of Example 6 except that the pH was initially adjusted to 12.0. An 81.8% yield of glyphosate salts was obtained.

EXAMPLE 12

Reaction was again carried out under the conditions of Example 6 except that the pH was initially adjusted to 12.7. A 36.9% yield of glyphosate salts was obtained.

EXAMPLE 13

Reaction of glycine and formylphosphonic acid was carried out under the conditions described in Example 6 except that the initial pH was 4.0. A 27% yield of glyphosate was obtained.

EXAMPLE 14

Reaction was carried out under the conditions of Example 6 except the pH was initially adjusted to 3.0. A 20% yield of glyphosate was obtained.

EXAMPLE 15

Reaction of glycine and formylphosphonic acid was carried out under the conditions of Example 2 except that the pH was initially adjusted to 8.0 and hydrogen gas was continuously bubbled through the liquid phase at atmospheric pressure. After 18 hours of reaction, a 65.9% yield of glyphosate was obtained.

Set forth in Table I below is a summary of the data for yield as a function of pH for reductive alkylation of glycine with formylphosphonic acid at various pH levels.

TABLE I

| Example | pH | Yield (%) |
|---|---|---|
| 2 | 7.0 | 91.0 |
| 3 | 6.0 | 78.0 |
| 6 | 8.0 | 93.9 |
| 9 | 11.0 | 95.0 |
| 10 | 10.0 | 90.0 |
| 11 | 12.0 | 81.8 |
| 12 | 12.7 | 36.9 |
| 13 | 4.0 | 27.0 |
| 14 | 3.0 | 20.0 |

A plot of yield as a function of pH as generated by computer using regression analysis is set forth in FIG. 1.

EXAMPLE 16

Glycine and formylphosphonic acid were reacted in accordance with the conditions described in Example 2 except the pH was initially adjusted to 8.0 and the catalyst was 1% palladium on carbon (0.5 g). After 20 hours of reaction, 2.54 g of glyphosate had been produced representing a 70.5% yield.

EXAMPLE 17

Reaction was carried out in the manner described in Example 16 except the catalyst was osmium metal powder (0.1 g). The yield of glyphosate salt after 16 hours was 29.2%.

EXAMPLE 18

Reaction was carried out in the manner described in Example 16 except the catalyst utilized was 5% platinum on carbon (0.5 g). After 16 hours the yield of glyphosate was 71.6%.

EXAMPLE 19

Reaction was carried out in the manner described in Example 16 except the catalyst utilized was 1% rhodium on graphite (0.5 g). After 20 hours the reaction was terminated and the product analyzed. The yield of glyphosate salt was 37.7%.

EXAMPLE 20

Reaction was carried out in the manner described in Example 16 except the catalyst was palladium oxide hydrate (2.0 g). A 57.4% yield of glyphosate salt was found.

EXAMPLE 21

Reaction was carried out in the manner described in Example 16 except the catalyst was ruthenium metal powder (0.5 g). After 16 hours of reaction, the yield of glyphosate was 42.3%.

EXAMPLE 22

Reaction was carried out in the manner described in Example 16 except that the catalyst was iridium dioxide (0.5 g). A 34.4% yield of glyphosate was obtained.

EXAMPLE 23

Reaction of formylphosphonic acid and glycine was carried out in the manner described in Example 16 except that the catalyst was 1% palladium on alumina (0.5 g, 3.2 mm pellets). A 34% yield of glyphosate was obtained.

EXAMPLE 24

Reaction was carried out in the manner described in Example 16 except the catalyst was rhodium (III) oxide (0.5 g). After 16 hours of reaction, the yield of glyphosate was 35.1%.

EXAMPLE 25

Reaction was carried out in the manner described in Example 16 except the catalyst was 0.5% platinum on alumina (1.0 g). A 52.9% yield of glyphosate was found.

EXAMPLE 26

Reaction was carried out in the manner described in Example 16 except the catalyst was ruthenium metal powder (0.5 g). After 16 hours of reaction, a 46.3% yield of glyphosate was found.

EXAMPLE 27

Glycine (1.14 g, 0.015 mole) and formylphosphonic acid (5.0 g of a 32% solution, 0.015 mole) were taken up in water and the pH adjusted to 8.0 by addition of 2.5N NaOH. This solution was placed in the cathode compartment of a divided cell. The anode chamber contained 0.1M KOAc solution. The cathode was mercury and the anode was a platinum screen. The cathode potential was held at $-1.2$ v vs. a sce reference electrode. A total of $5.7 \times 10^{-3}$ Faraday of current was passed. Analysis of the catholyte revealed that 1.1 g of glyphosate had been produced for a 43% yield based on consumed glyphosate.

EXAMPLE 28

The electrochemical reductive alkylation of glycine by formylphosphonic acid was carried out as described in Example 27 except the reaction was carried out in an undivided cell. A 65% yield of glyphosate was found.

EXAMPLE 29

The reductive alkylation of glycine by formylphosphonic acid was carried out as described in Example 27 except that a constant current of 50 mA was employed and the pH was maintained at 8.0 throughout the electrolysis by addition of dilute hydrochloric acid. Current was passed for 2.5 hours and the catholyte was analyzed for glyphosate by HPLC. A total of 1.53 g of glyphosate was found (39% yield).

EXAMPLE 30

Glycine (1.14 g, 0.015 mole) and 2 equivalents of formylphosphonic acid (6.5 g of a 50% solution, 0.03 mole) were reacted according to Example 2. After allowing the reaction to proceed overnight, the reaction mixture was analyzed by HPLC. A 71% yield of the tertiary amine product, glyphosine, $HO_2CCH_2N(CH_2PO_3H_2)_2$ was observed.

As various changes could be made in the above methods and processes without departing from the scope of the invention, it is intended that all matter contained in the above description or shown in the accompanying drawings shall be interpreted as illustrative and not in a limiting sense.

What is claimed is:

1. A process for preparing a compound of the formula

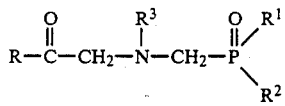

wherein R can be hydrogen and R, $R^1$, and $R^2$ are independently selected from the group consisting of —OH; —SH;
- —$NR^4R^5$ wherein $R^4$ and $R^5$ are independently selected from the group consisting of hydrogen, alkyl, and hydroxyalkyl having 1 through 4 carbon atoms, alkenyl having 2 through 4 carbon atoms, and $R^4$ and $R^5$ together with the nitrogen atoms can form a heterocyclic ring;
- —$OR^6$ and $SR^6$ wherein $R^6$ is selected from the group consisting of monovalent hydrocarbon groups, monovalent hydrocarbonoxyhydrocarbon groups each containing from 1 to 18 carbon atoms, halogenated monovalent hydrocarbon groups, halogenated monovalent hydrocarbonoxyhydrocarbon groups each containing from 1 to 18 carbon atoms and from 1 to 3 halogens, and groups having the formula

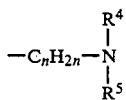

wherein n is from 1 to 4, and $R^4$ and $R^5$ are as defined above;
—$OR^7$ wherein $R^7$ is a herbicidally acceptable salt-forming cation; and
$R^3$ is hydrogen or alkyl,
the process comprising:
condensing a precursor primary or secondary amine corresponding to the formula

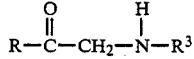

where R and $R^3$ are as defined above, in an aqueous reaction medium, with carbonyl compound, or hydrate or acetal thereof, said carbonyl compound corresponding to the Formula (III) or (IV)

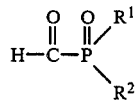

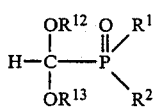

wherein $R^1$ and $R^2$ are as defined above, $R^{12}$ and $R^{13}$ are independently selected from hydrogen, alkyl, hydroxyalkyl having 1 to 4 carbon atoms, alkenyl and alkyl having 2 to 4 carbon atoms joined through the oxygen atoms to form a cyclic acetal, aryl, substituted aryl, or heterocyclic moieties; and reducing the condensation product without isolation to produce a compound of Formula (I).

2. The process of claim 1 wherein at least one of R, $R^1$, and $R^2$ is $OR^7$ wherein R is a salt-forming cation selected from the group consisting of alkali metals, alkaline earth metals, copper, zinc, manganese, nickel, ammonium, aliphatic ammonium, phosphonium, aliphatic phosphonium, aliphatic sulfonium, and primary aryl ammonium.

3. A process as set forth in claim 1 wherein the pH of said reaction medium is between about 5.5 and about 12.0 during said condensation and reduction reactions.

4. A process as set forth in claim 3 wherein said pH is adjusted between about 7.0 and about 12.0 during said reactions by addition of a base.

5. A process as set forth in claim 1 wherein the concentration of each of said precursor amine and said carbonyl compound reactants in said aqueous medium is between about 2% and about 20% by weight.

6. A process as set forth in claim 5 wherein the molar ratio of said carbonyl compounds to said precursor amine is between 1.0 and about 1.2.

7. A process as set forth in claim 1 wherein said reduction is carried out electrochemically.

8. A process as set forth in claim 7 wherein said reduction is carried out using a mercury electrode.

9. A process as set forth in claim 7 wherein the reduction is carried out in a cell having a porous barrier between cathode and anode, and said aqueous medium containing said precursor amine and said carbonyl compound comprises the catholyte in said cell.

10. A process as set forth in claim 7 wherein the cell is operated at a current density of between about 0.001 and about 0.5 amperes per $cm^2$.

11. A process as set forth in claim 1 wherein said reduction reaction is carried out by catalytic hydrogenation.

12. A process as set forth in claim 11 wherein said catalyst is selected from the group consisting of platinum, palladium, osmium, iridium, rhodium, ruthenium, nickel, cobalt, copper, zinc, and compounds of said metals.

13. A process as set forth in claim 12 wherein said catalyst comprises a platinum group metal on a carbon support.

14. A process as set forth in claim 12 wherein said catalyst comprises a nickel or a nickel compound.

15. A process as set forth in claim 14 wherein said catalyst comprises Raney nickel.

16. A process as set forth in claim 12 wherein said catalyst comprises a water-soluble compound.

17. A process as set forth in claim 1 wherein $R^3$ is H and R, $R^1$, and $R^2$ are OH.

18. A process as set forth in claim 1 wherein one of R, $R^1$ and $R^2$ is $OR^7$, and $R^7$ is selected from a herbicidally acceptable salt-forming cation which renders the compound more readily soluble in water.

19. A process as set forth in claim 4 wherein said base comprises a tertiary, secondary, or primary amine.

20. A process as set forth in claim 1 wherein $R^3$ is represented by the formula

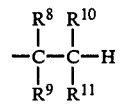

wherein $R^8$, $R^9$, $R^{10}$, and $R^{11}$ are independently selected from the group consisting of hydrogen, alkyl $C_{1-6}$, aryl, and substituted aryl provided no more than two of $R^8$, $R^9$, $R^{10}$, and $R^{11}$ are aryl or substituted aryl.

21. A process as set forth in claim 20 wherein $R^3$ is isopropyl.

* * * * *